United States Patent [19]

Ward et al.

[11] Patent Number: 5,501,986

[45] Date of Patent: Mar. 26, 1996

[54] PIEZOELECTRIC SPECIFIC BINDING ASSAY WITH MASS AMPLIFIED REAGENTS

[75] Inventors: Michael D. Ward, Newark; Richard C. Ebersole, Wilmington, both of Del.

[73] Assignee: E. I. Du Pont de Nemours and Company, Wilmington, Del.

[21] Appl. No.: 283,475

[22] Filed: Jul. 28, 1994

Related U.S. Application Data

[63] Continuation of Ser. No. 908,505, Jun. 30, 1992, abandoned, which is a continuation of Ser. No. 409,886, Sep. 20, 1989, abandoned, which is a continuation-in-part of Ser. No. 178,367, Apr. 6, 1988, abandoned.

[51] Int. Cl.$^6$ .................................................. G01N 33/531
[52] U.S. Cl. ........................... 436/525; 436/807; 436/808
[58] Field of Search ............................. 436/525, 806–807

[56] References Cited

U.S. PATENT DOCUMENTS

| | | | |
|---|---|---|---|
| 4,236,983 | 12/1980 | Rice | 23/230 |
| 4,313,734 | 2/1982 | Leuvering | 436/525 |
| 4,314,821 | 2/1982 | Rice | 23/230 |
| 4,735,906 | 4/1988 | Bastiaans | 436/806 X |

FOREIGN PATENT DOCUMENTS

| | | |
|---|---|---|
| 0215669 | 3/1987 | European Pat. Off. . |
| 0276142 | 7/1988 | European Pat. Off. . |
| 0295965 | 12/1988 | European Pat. Off. . |
| 3733986 | 4/1987 | Germany . |

OTHER PUBLICATIONS

Shors, et al., J. Biomed. Mater. Res., vol. 6, pp. 565–570 (1972).
Roederer, et al., Anal. Chem., vol. 55, pp. 2333–2336 (1983).
Ngen–Ngwainbi, et al., J. Mat. Chem. Soc., vol. 108, pp. 5444–5447 (1986).
Hainfeld, Science, vol. 236, pp. 450–453, (1987).
Grabbe, et al., G. Electroanal. Chem., vol. 223, pp. 67–78 (1987).
Ollerich, *J. Clin. Chem. Clin Biochem.* 22(12) (1984).

*Primary Examiner*—Lyle A. Alexander

[57] ABSTRACT

A piezoelectric crystal-based specific binding assay in which a sol is used to increase the mass of binding reagents to amplify responses to analyte.

4 Claims, 3 Drawing Sheets

PIEZOELECTRIC SPECIFIC BINDING ASSAY WITH MASS AMPLIFIED REAGENTS

This is a continuation of application Ser. No. 07/908,505 filed Jun. 30, 1992, now abandoned, which is a continuation of application Ser. No. 07/409,886 filed 20 Sep. 1989, now abandoned, which is in turn a continuation-in-part of application Ser. No. 07/178,367, filed 06 Apr. 1988 now abandoned.

FIELD OF THE INVENTION

The present invention relates to piezoelectric crystal-based specific binding assays, such as immunoassays and nucleic acid probe assays, in which the binding between a piezoelectric crystal and a sol particle is either inhibited or augmented by the addition of a sample suspected of containing an analyte of interest.

BACKGROUND OF THE INVENTION

The use of quartz crystal microbalances (also known as piezoelectric oscillators) in immunoassays has been described previously. These devices consist of single crystal wafers sandwiched between two electrodes. The electrodes are provided with means for connecting these devices to an external oscillator circuit that drives the quartz crystal at its resonant frequency. This frequency is dependent on the mass of the crystal, as well as the mass of any layers confined to the electrode areas of the crystal. Thus, the frequency is altered by changes in mass on the surface of the electrodes or in any layers on those electrodes. In general, the change in resonant frequency of these devices can be correlated to the amount of mass change; if the quartz crystal microbalance and any attached layers obey rigid-layer behavior, the mass change can be determined from the frequency change by the Sauerbrey relationship $$\Delta f = -\frac{2f_0^2 \Delta m}{A \sqrt{\rho_q \mu_q}}$$

where $\Delta f$ is the measured frequency shift, $f_0$ the parent frequency of the quartz crystal, $\Delta m$ the mass change, $A$ the piezoelectrically active area, $p_q$ the density of quartz (2.648 g cm$^{-3}$) and $u_q$ the shear modulus ($2.947 \times 10^{11}$ dynes cm$^{-2}$ for AT-cut quartz).

Shons et al. describe a piezoelectric quartz crystal microbalance which has been modified for the determination of antibody activity in solution. A quartz crystal, precoated with antigen, is exposed to antisera of varying concentration and specificity. Antisera specific for the antigen coating will form an additional protein layer on the crystal. The thickness of the antibody layer, measured by the frequency shift of the dry crystal, is proportional to the concentration of specific antibody in solution. [J. Biomed. Mater. Res., Vol. 6, pp. 565–570 (1972)]

U.S. Pat. No. 4,236,893, issued to Rice on Dec. 2, 1980, discloses a method for the determination of a particular subclass of antibody. The method utilizes a piezoelectric oscillator having bound to its surface an antigen specific for the antibody to be determined. The antigen-coated oscillator is exposed to a solution containing an unknown amount of the antibody. After the antibody in the solution is attached to the antigen on the oscillator, the oscillator is exposed to a so-called sandwiching substance which selectively binds to a specific subclass of the antibody being determined. The frequency of the oscillator is measured in the dry state before and after exposure to the sandwiching substance. The change in frequency is related to the amount of the subclass of antibody bound to the oscillator, and the amount of the subclass of antibody in the solution can be determined by reference to a standard curve.

Roederer et al. disclose an in-situ immunoassay using piezoelectric quartz crystals, specifically, surface acoustic wave devices. Goat anti-human IgG was immobilized on the quartz crystal surface with a coupling agent. The piezoelectric crystals were then placed in an electric oscillator circuit and tested for detection of the antigen human IgG. Detection was based upon the fact that surface mass changes by adsorption are reflected as shifts in the resonant frequencies of the crystals. The authors concluded that the method suffers from both poor sensitivity and poor detection limits. The authors also concluded that the antigen to be detected must be of high molecular weight; low molecular weight analytes cannot be directly detected by this methodology. [Analytical Chemistry, Vol. 55, (1983)]

Ngeh-Ngwainbi et al. describe the use of piezoelectric quartz crystals coated with antibodies against parathion which are used for the assay of parathion in the gas phase. When the coated antibody binds with parathion by a direct reaction in the gas phase, the resulting mass change on the crystal generates a frequency shift proportional to the concentration of the pesticide. [J. Mat. Chem. Soc., Vol. 108, pp. 5444–5447 (1986)]

European patent application 0 215 669, published Mar. 25, 1987, discloses an analytical device and method for the in-situ analysis of biochemicals, microbes and cells. Again, the method is predicated on a resonant frequency change caused by a weight change on the surface of a piezoelectric crystal on which are immobilized receptor materials specific for the analyte to be detected.

Grabbe et al. describe a quartz crystal resonator, used in conjunction with cyclic voltammetry, to study the binding of human IgG and anti-IgG at a silver electrode. [G. Electroanal. Chem. Vol. 223, pp. 67–78 (1987)]

As discussed by Roederer et al., piezoelectric crystal-based immunoassays in which mass change is attributable only to the immunological reaction between an antigen and an antibody can, under certain circumstances, suffer from poor sensitivity and poor detection limit. Consequently there is a need in the art for a piezoelectric crystal-based specific binding assay in which the reaction between a binding agent and its ligand can be amplified to provide a more sensitive and reliable assay. There is a further need for an assay without added procedural complexity.

SUMMARY OF THE INVENTION

These needs are met by the present invention. In one aspect, a process is described for measuring the concentration of an analyte utilizing massive sol particles that have been modified to contain binding agents which make the particles capable of binding to the surface of a quartz crystal microbalance which also has been modified with a binding agent. The modified quartz crystal microbalance is referred to herein as a biologically modified quartz crystal microbalance, or BMQCM. The quartz crystal microbalance may have at least one of its surfaces modified by any combination of priming, coating or reagent layers. Binding of the sol reagent to the BMQCM results in a mass change at the surface of the BMQCM, which in turn produces a corresponding change in the resonant frequency of the quartz crystal. The actual assay can be performed in a competitive mode wherein analyte binds to either the binding agent on the modified sol particle or to the binding agent on the surface of the BMQCM, thereby inhibiting the binding of the sol to the binding agent on the BMQCM. In this case, the response of the BMQCM is inversely proportional to the concentration of the analyte. Alternatively, the assay can be performed in a so-called sandwich mode, wherein the modified sol particle indirectly binds to the surface of the BMQCM by complexation to an analyte which, itself, is indirectly bound to a quartz crystal microbalance. In both modes of operation, the large effective mass of the modified sol particles results in a large change in mass upon binding with the BMQCM, and hence a large shift in resonant frequency. Furthermore, frequency measurements can be made in the presence of the sol reagent without the need for additional processing to separate bound and free sol reagent.

BRIEF DESCRIPTION OF THE DRAWING

The drawing consists of four figures.

DETAILED DESCRIPTION OF THE INVENTION

Figure 1:
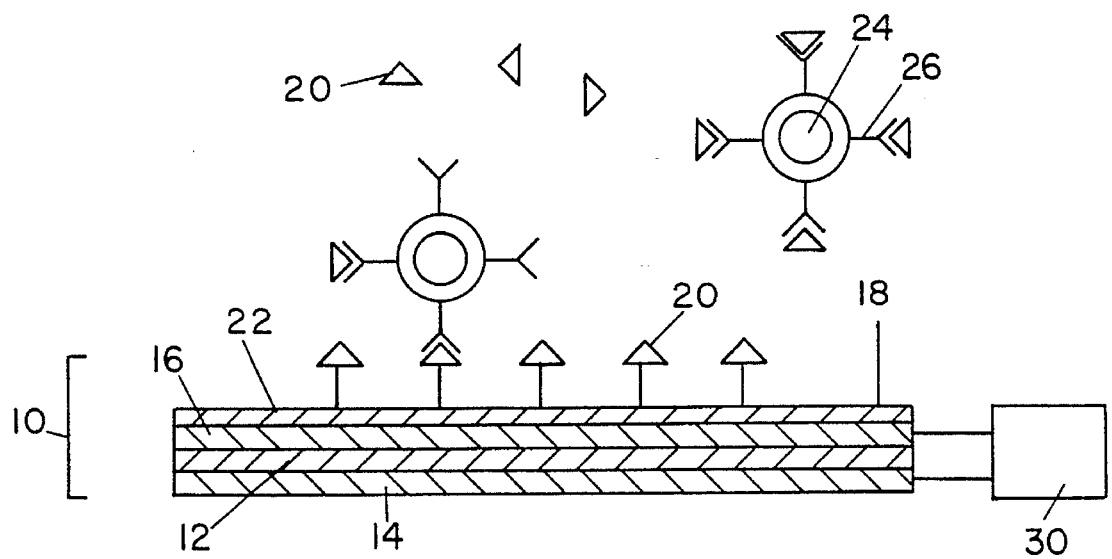
FIGS. 1 to 3 depict various modes of carrying out the present invention.
Figure 1A:
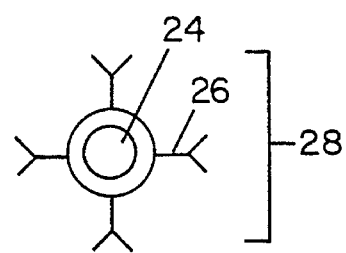

The invention may be understood by reference to the Drawing, wherein like reference numerals are used to indicate like elements.

Referring now to FIG. 1, there is seen a biologically modified quartz crystal microbalance (BMQCM) indicated generally by the reference numeral 10. The BMQCM comprises a quartz crystal wafer 12 sandwiched between two electrodes 14, 16. Attached to one surface 18 of the BMQCM 10 is a first member of a specific binding pair 20, referred to herein by the acronym "MOSBP-1". The surface 18 may be formed by modifying the surface of electrode 16 with priming or coating layers 22 that serve to enhance attachment of the MOSBP-1 20. MOSBP-1 20 may be attached to the quartz crystal microbalance surface 18 by physical adsorption or covalent attachment. Other well-known chemical techniques, such as glutaraldehyde crosslinking applied to protein, can also be utilized for attachment of MOSBP-1 to the quartz crystal microbalance.

Layers 22 may be formed from polymer films and silane reagents that serve to enhance the attachment of MOSBP-1 to the quartz crystal either by imparting hydrophobicity or providing functional groups for covalent attachment. An example of a polymer film is polystyrene, which can be applied by conventional methods, such as spin coating. Higher surface area coatings for greater reagent coverage can be achieved by fabrication of irregular and three dimensionally shaped surfaces, such as by aerosol application or lithography. Suitable silanes include the general class of alkyltrichlorosilanes, which covalently bind to the metal and glass surfaces of the quartz crystal microbalance by M-O-Si and Si-O-Si linkages, respectively.

The BMQCM having MOSBP-1 bound thereto is exposed to a solution (not shown) containing a sol particle 24 modified with a second member of a specific binding pair 26, referred to herein by the acronym "MOSBP-2", whose binding sites are complementary to those of MOSBP-1. The reagent comprised of the sol particle 24 and MOSBP-2 is referred to herein as a "modified sol particle" 28. The modified sol particle 28 is capable of complexing with MOSBP-1. The resulting increase in mass due to complexation at the surface of the BMQCM will result in a change in resonant frequency, as measured by an external circuit 30.

Suitable reagents that can serve as MOSBP-1 20 include those which are capable of participating in complexation reactions with MOSBP-2. Preferred reagents include without limitation members of antibody/antigen pairs, lectins, chelating agents, binding proteins, DNA and RNA polynucleic acids and cell receptors. The choice of MOSBP-1 will depend on the analyte to be measured, as it must contain similar, if not identical, binding sites as the analyte of interest.

Suitable reagents that can serve as MOSBP-2 include those which are complementary to MOSBP-1 and, therefore, capable of participating in complexation reactions with MOSBP-1, including members of antibody/antigen pairs, lectins, chelating agents, binding proteins, DNA and RNA polynucleic acids and cell receptors.

Suitable analytes include proteins, hormones, enzymes, antibodies, drugs, carbohydrates, nucleic acids, etc.

Generally, suitable sol particles include those having a density exceeding that of the binding agent to which the sol particles are attached. Specifically, the so-called areal density of the modified sol particle 28, when bound to the BMQCM surface 18 must exceed the areal density of MOSBP-2, alone. Preferred sol particle diameter is in the range of 5 to 100 nm. Preferred reagents can include single element systems such as gold and lead, and binary systems such as CdS, ZnS, $CrO_2$, iron oxide and $TiO_2$. High density polymers may also be suitable.

Modified sol particles can be made by well-known methods, including those described in the following references:

1. Muller et al., J. Immunol. Methods, 37, 185 (1980);
2. Roth, *Techniques in Immunocytochemistry*, Vol. 2, p. 285, Ed. Bullock et al., Academic Press (1983);
3. Hainfeld, Science, 236, 450 (1987).

The actual assay depicted in FIG. 1 is performed in a competitive mode, in which the analyte, 20, possesses binding sites identical to those of MOSBP-1 20 on the BMQCM surface. Specific binding of the analyte to the modified sol particle 28 deactivates the MOSBP-2 modified sol particle, thereby inhibiting its binding to MOSBP-1 on the surface of the BMQCM. The resonant frequency change due to the binding of modified sol particle 28 to MOSBP-1 on the surface of the BMQCM is, therefore, not as large as it would be in the absence of analyte, as described earlier. The diminution in frequency is proportional to the concentration of analyte in solution. A standard reference curve can be used to quantitatively determine the analyte concentration. The larger changes in mass for sol particle binding, compared to simple binding of MOSBP-2, alone, result in larger differences in frequency change for a given amount of binding, thereby increasing the overall sensitivity and detection limits of the piezoelectric assay. It should be appreciated that the addition of the modified sol particle 28 reagent and the analyte 20 can be performed either sequentially or simultaneously.

Figure 2:
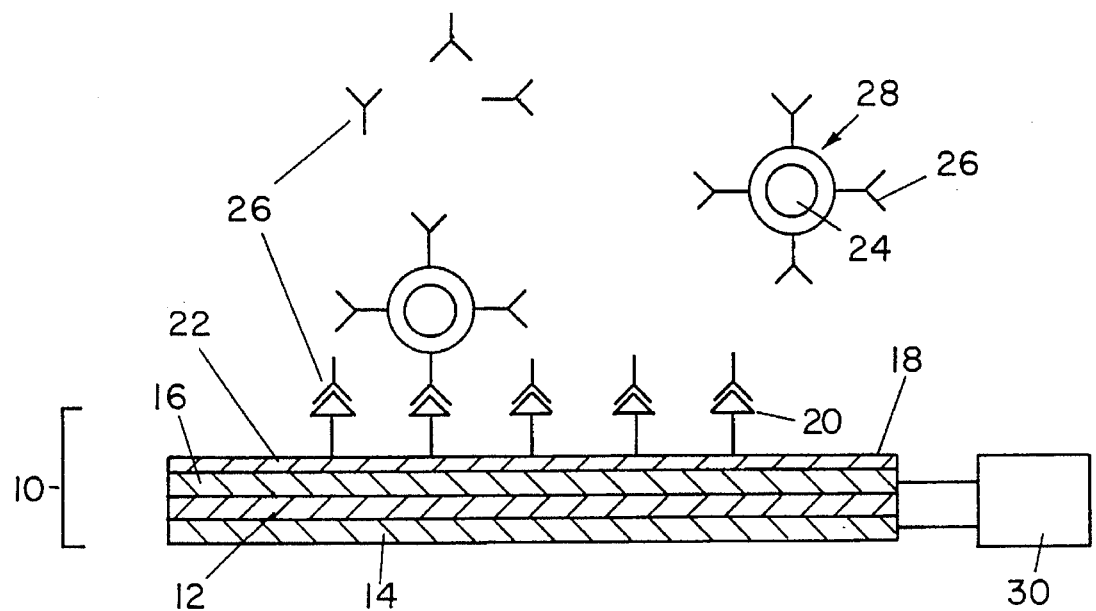

An alternative embodiment, also performed in a competitive mode, is depicted in FIG. 2. Here, the analyte 26 is the same as or analogous to the MOSBP-2 26 on the sol particle 24. The resonant frequency change due to specific binding of the modified sol particle 28 to MOSBP-1 on the surface of the BMQCM is decreased by specific binding of the analyte 26 to MOSBP-1 20. The resonant frequency change due to binding of modified sol particle 28 to MOSBP-1 20 on the surface of the BMQCM 10 is, therefore, not as large as it would be in the absence of analyte 26 as described earlier, reflecting the difference in mass between the modified sol particle 28 and MOSBP-2 26. The diminution in resonant frequency is proportional to the concentration of analyte in solution. A standard reference curve can be used to quantitatively determine the analyte concentration. It should be appreciated that the addition of the modified sol particle reagent 28 and the analyte can be performed either sequentially or simultaneously.

Suitable reagents that can serve as MOSBP-1 20 include those reagents which are capable of participating in complexation reactions with MOSBP-2. Preferred reagents include without limitation members of antibody/antigen pairs, lectins, chelating agents, binding proteins, DNA and RNA polynucleic acids and cell receptors. The choice of MOSBP-1 will depend on the analyte to be measured, as it must contain sites that are complementary to those of the analyte of interest.

Suitable reagents that can serve as MOSBP-2 include those which are complementary to MOSBP-1 and, therefore, capable of participating in complexation reactions with MOSBP-1, including members of antibody/antigen pairs, lectins, chelating agents, binding proteins, DNA and RNA polynucleic acids and cell receptors.

Suitable analytes include proteins, hormones, enzymes, antibodies, drugs, carbohydrates, nucleic acids, etc.

Preferred sols include those previously described.

Figure 3:
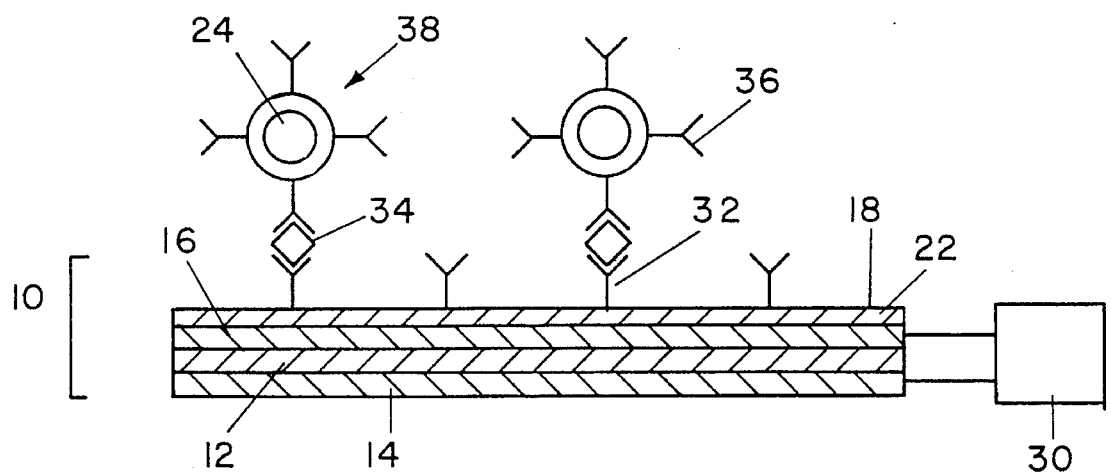
Figure 4:
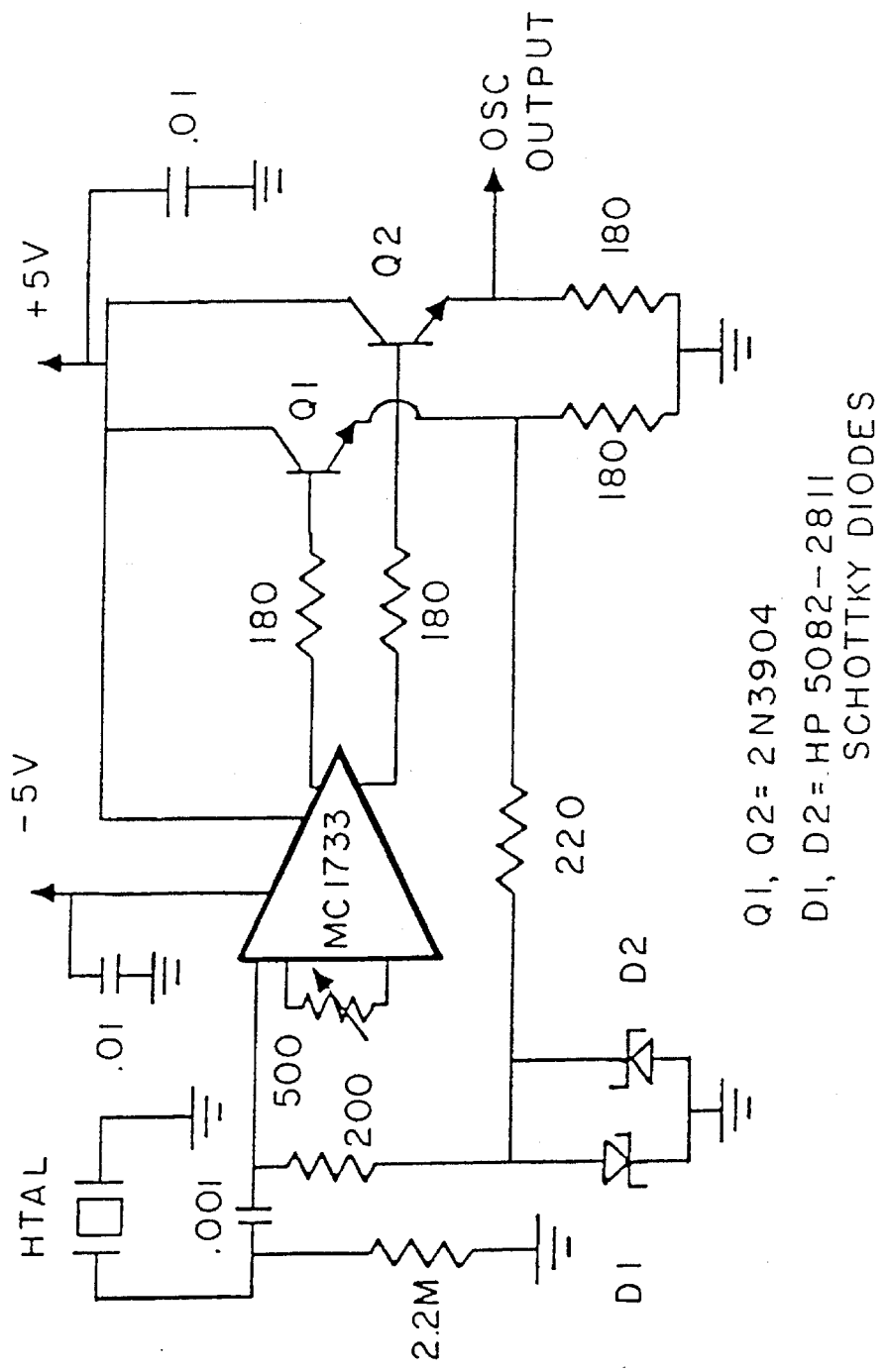
FIG. 4 depicts suitable circuitry for measuring the resonant frequency of the BMQCM.

A third embodiment is depicted in FIG. 3, in which the assay is performed in a so-called sandwich mode, instead of a competitive mode. In this mode, the BMQCM 10 is comprised of the quartz crystal 12, metal electrodes 14 and 16, any modifying layers 22 and a first binding reagent 32, referred to herein as BR-1, attached thereto. The BMQCM is exposed to a sample containing analyte 34, followed by washing to remove nonspecifically bound analyte. The BMQCM 10 containing bound analyte 34 is then exposed to a solution of a reagent 38 comprising the sol particle 24 and a second binding reagent 36, referred to herein as BR-2. The modified sol particle 38 specifically binds to the analyte 34 on the surface of the BMQCM, resulting in a change in mass, and thereby a change in resonant frequency. The frequency change is larger than that realized for simple direct binding of BR-2 36 (without sol particle) owing to the significantly larger density of the sol particle 24 compared to BR-2. A standard reference curve can be used to quantitatively determine the analyte concentration. It should be appreciated that the addition of the analyte 34 and the modified sol particle 38 can be performed either sequentially or simultaneously.

Suitable reagents that can serve the role of BR-1 32 include those reagents which are capable of participating in complexation reactions with analyte 34. Preferred reagents include antibodies, lectins, chelating agents, binding proteins, DNA and RNA polynucleic acids and cell receptors. Suitable reagents that can serve the role of BR-2 are identical to those described for BR-1 provided they are also capable of participating in complexation reactions with the analyte 34 after it is bound to BR-1. It should be appreciated that BR-1 and BR-2 may be the same or different.

Suitable analytes include proteins, hormones, enzymes, antibodies, drugs, carbohydrates, nucleic acids, etc.

Preferred sols include those previously described.

It will be appreciated that this third embodiment is especially suitable for detecting analytes comprising specific gene sequences in polynucleic acids such as DNA and RNA. For such analytes, BR-1 will be a synthetic polynucleotide complementary to the sequence to be detected. BR-2 will also be a synthetic polynucleotide complementary to a separate sequence contained within the polynucleic acid to be detected.

The present invention can be embodied in diagnostic kits comprising crystals treated with the desired reagent and any modifying layers, and an oscillator circuit with direct readout of the resonant frequency of the quartz crystal microbalance. In typical use, the analyte solution, for example patient serum, would be added to a compartment containing the BMQCM, followed by addition of the sol reagent. The frequency will be proportional to the concentration of the analyte, and reference to a standard curve can be used to determine its concentration. The preferred mode of operation would include the use of a reference crystal in a separate compartment. The reference crystal should also be modified with the same reagents. In this mode, the sol reagent is added to both the test and reference compartment. The difference in frequency shift between the two compartments then reflects the concentration of analyte in solution.

EXAMPLE

The following nonlimiting example illustrates the basic principles and unique advantages of the present invention.

Assay of Human IgG (hIgG)

This example illustrates the invention by showing that analyte can be used to alter crystal frequency by affecting particle binding, as depicted in FIG. 1. Furthermore, the example illustrates that measurement of particle binding can be accomplished without need for washing the crystal to separate "bound" from "free" particles as required in conventional immunoassay procedures. Assay procedures can thus be simplified.

Crystal/hIgG preparation was accomplished by first coating the quartz crystal microbalance (QCM) with a layer (ca. 0.5 u) of polystyrene (PS) by spin coating the crystal with a 10% solution of PS in o-chlorotoluene. After air drying, a protein was adsorbed on the QCM surface by equilibrating the QCM in 1.5 mL of a solution (0.2%) of hIgG in a phosphate buffered saline solution (PBS) for 2 hours at 4° C. Before use, the QCM was washed free of unbound hIgG using three washes of PBS buffer and then stored at 4° C. in PBS buffer until use.

Following preparation of the crystal/hIgG, a single BMQCM was treated first with 0.4 mL of a solution of 1% BSA in PBS buffer to establish a base line crystal response. Gold sol reagent [prepared by diluting 200 uL of a gold sol (15 nm)/protein A (11 ug/mL) suspension purchased from E-Y Laboratories Inc. (San Mateo, Calif.) with 300 uL of a solution of 1% BSA in PBS buffer] was then added to the BMQCM, and the rate of particle reagent binding was followed at room temperature until the rate of particle binding approached steady state. This established the rate of particle binding in the absence of hIgG analyte. The rate was determined to be 9 Hz/min. (Higher responses, i.e. 88 Hz/min, can be achieved for surfaces prepared with gluteraldehyde crosslinked hIgG on the BMQCM surface). A second crystal treated with hIgG, as above, was first exposed to 0.4 mL of 1% BSA in PBS buffer containing hIgG (200 ug/mL) to establish a base line frequency response. Gold sol/protein A reagent (0.6 mL) was then added and the rate of particle binding monitored. In this case, no change in frequency was observed. The marked differences between the steady rates of frequency change in the presence and absence of hIgG clearly demonstrates particle reagent attachment to the crystal.

The invention is defined by the following claims, although it will be appreciated by those skilled in the art that various modifications can be made without departing from the spirit thereof.

What is claimed is:

1. A method for detecting an analyte suspected of being present in a sample, comprising the steps of:
   (1) forming a reaction system comprising:
      (i) a QCM capable of a change in resonant frequency having a first member of a specific binding pair attached to the surface thereof;
      (ii) a gold sol particle attached to a second member of the specific binding pair, the gold sol particle
         a) having a diameter between about 5 to 100 nm,
         b) and wherein the second member of the specific binding pair attached to the gold sol particle is capable of binding to the first member of the specific binding pair which is attached to the QCM surface;
         c) wherein the areal density of the gold sol particle exceeds the areal density of the member of binding pair to which the sol particle is attached; and
      (iii) an analyte receptor site residing on either the first member of the specific binding pair or on the second member of the specific binding pair;
   (2) adding to the reaction system a sample suspected of containing an analyte, whereby the analyte specifically reacts with either the first or second member of the specific binding pair, thereby preventing the binding of the first member to the second member whereby such prevention of binding inhibits the attachment of the gold sol particle to the QCM and thereby effects a change in said resonant frequency of said QCM;
   (3) measuring the change in resonant frequency; and
   (4) correlating the change in resonant frequency obtained in step (3) with the amount of the analyte suspected of being present in the sample.

2. The method of claim 1 wherein the first member of the specific binding pair is an antigen for said antibody.

3. The method of claim 2 wherein the second member of the specific binding pair is an antigen for said antibody.

4. A method for detecting an analyte suspected of being present in a sample, comprising the steps of:
   (1) forming a reaction system comprising:
      (i) a QCM capable of a change in resonant frequency having a first binding reagent attached to a surface thereof;
      (ii) a gold sol particle bound to a second binding reagent, said first and second binding reagents being the same or different, whereby the gold sol particle is incapable of specific binding to the QCM surface, and further wherein the sol particle has a diameter between about 5 and 100 nm wherein the areal density of the gold sol particle exceeds the areal density of the member of binding pair to which the sol particle is attached; and
      (iii) an analyte receptor site on both the first binding reagent and the second binding reagent;
   (2) adding to the reaction system a sample suspected of containing an analyte, whereby the analyte binds to both the first and second binding reagents thereby causing the binding of the gold sol particle to the QCM surface and effecting a change in the resonant frequency of the QCM;
   (3) measuring the change in resonant frequency; and
   (4) correlating the change in resonant frequency obtained in step (3) with the amount of the analyte suspected of being present in the sample.

* * * * *